United States Patent [19]

Kikuchi

[11] Patent Number: 4,853,772
[45] Date of Patent: Aug. 1, 1989

[54] ELECTRONIC ENDOSCOPE APPARATUS HAVING ISOLATED PATIENT AND SECONDARY CIRCUITRY

[75] Inventor: Kenichi Kikuchi, Hachioji, Japan

[73] Assignee: Olympus Optical Co., Ltd., Tokyo, Japan

[21] Appl. No.: 158,958

[22] Filed: Feb. 22, 1988

[30] Foreign Application Priority Data

Jun. 24, 1987 [JP] Japan ............................ 62-158427
Feb. 26, 1988 [JP] Japan ............................ 63-043578

[51] Int. Cl.$^4$ ............................................. H04N 9/18
[52] U.S. Cl. ................................. 358/98; 358/903; 128/4; 128/6; 128/908; 354/62
[58] Field of Search ............ 358/98, 903; 128/4, 128/6, 303.15, 901, 908; 354/62; 250/551; 455/602

[56] References Cited

U.S. PATENT DOCUMENTS

| | | | |
|---|---|---|---|
| 4,384,775 | 5/1983 | Hosoda | 354/62 |
| 4,473,841 | 9/1984 | Murakoshi et al. | 358/98 |
| 4,519,391 | 5/1985 | Murakoshi | 128/4 |
| 4,633,304 | 12/1986 | Nagasaki | 358/98 |
| 4,656,503 | 4/1987 | Hynecek | 358/44 |
| 4,706,118 | 11/1987 | Kato et al. | 358/98 |
| 4,719,508 | 1/1988 | Sasaki et al. | 358/98 |
| 4,737,842 | 4/1988 | Nagasaki | 358/98 |

FOREIGN PATENT DOCUMENTS 57-198161 12/1982 Japan.
58-69528 4/1983 Japan.

Primary Examiner—Howard W. Britton
Assistant Examiner—John K. Peng
Attorney, Agent, or Firm—Armstrong, Nikaido Marmelstein Kubovcik & Murray

[57] ABSTRACT

This electronic endoscope apparatus comprises an endoscope provided with an imaging apparatus converting a light information of an object to be imaged to an electric signal and a signal processing apparatus processing the output signal of the imaging apparatus to be a video signal. The signal processing apparatus has an isolating device isolating and transmitting the information from the imaging apparatus from the patient circuit side to the secondary circuit side and a converting device converting the signal from the imaging apparatus to a signal adapted to be transmitted by the isolating device and delivering it to the isolating device.

21 Claims, 12 Drawing Sheets

FIG. 10A  R-Y  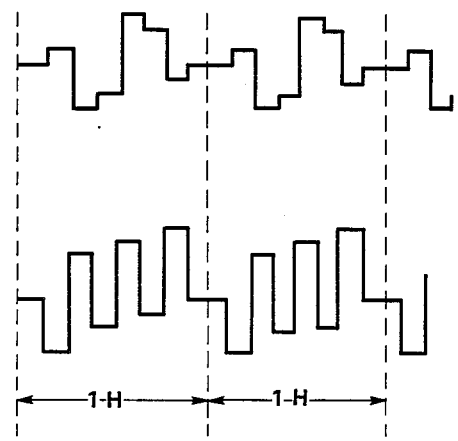
FIG. 10B  B-Y 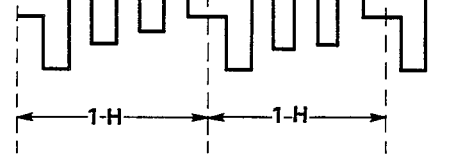

ELECTRONIC ENDOSCOPE APPARATUS HAVING ISOLATED PATIENT AND SECONDARY CIRCUITRY

BACKGROUND OF THE INVENTION

1. Field of the Invention:

This invention relates to an electronic endoscope apparatus wherein the patient circuit side and secondary circuit side are insulated from each other.

2. Related Art Statement:

Recently, there is extensively utilized an endoscope whereby organs within a body cavity can be observed by inserting an elongate insertable part into the body cavity or various curing treatments can be made as required by using a treating tool inserted through a treating tool channel.

There are also suggested various electronic endoscopes of a system wherein such solid state imaging device as a charge coupled device (CCD) is provided as an imaging means in the tip part of an insertable part so that a picture image information may be taken out as a photoelectrically converted electric signal.

Now, in the case of a medical electronic endoscope, a circuit part (patient circuit) inserted into the body of a patient and a circuit part (secondary circuit) connected to such peripheral device as a monitor must be isolated from each other.

FIG. 14 shows an example of the formation of such electronic endoscope apparatus.

In this drawing, the image of an object to be imaged is formed on a solid state imaging device 3 by an image forming optical system 2 and the signal photoelectronically converted by this solid state imaging device 3 is fed to a video signal processing circuit 5 through a cable 4. As this video signal processing circuit 5 is connected to such peripheral device as a monitor, the video signal must be isolated on the patient circuit side and secondary circuit side by an isolation circuit 6 within the video signal processing circuit 5.

There is such isolation system as a system wherein the output of the solid state imaging device 3 is passed directly through an isolation transformer or a system wherein, for example, in the case of a CCD, a signal taking the difference between a signal delaying the original signal by half the pixel sampling period and the original signal is passed through an isolation transformer to sample the effective signal part.

As such a Prior Art example mentioned above, one is disclosed in a Japanese utility model application Laid Open No. 198161/1982.

However, in the case of isolating the patient circuit and secondary circuit from each other, the output of the solid state imaging device has a low frequency component in the signal and therefore can not be directly passed through the isolation transformer. Also, in the case of the CCD output, the signal taking the delay difference can be passed through the isolation transformer. However, there is a problem that, when the signal is passed through the transformer, the high frequency component of the signal will attenuate and therefore no positive sampling will be able to be made.

Here, measures of reducing the noises of the solid state imaging device may be positively taken on the patient circuit side. In this case, there is a defect that, as the signal band is only a base band, the signal can not be transmitted with the isolation transformer.

OBJECT AND SUMMARY OF THE INVENTION

An object of the present invention is to provide an electronic endoscope apparatus wherein the patient circuit side and secondary circuit side can be well isolated from each other without deteriorating the picture quality.

Another object of the present invention is to provide an electronic endoscope apparatus wherein the patient circuit side and secondary circuit side can be well isolated from each other and the solid state imaging device output ca be processed to positively reduce noises.

A further object of the present invention is to provide an electronic endoscope apparatus wherein the patient circuit side and secondary circuit side can be well isolated from each other and few noises are mixed in.

The electronic endoscope apparatus of the present invention is provided with an endoscope provided with an imaging means converting a light information of an object to be imaged to an electric signal and a signal processing means processing the output signal of the above mentioned imaging means to be a video signal. The above mentioned signal processing means has an isolating means isolating and transmitting the information from the above mentioned imaging means to the secondary circuit side from the patient circuit side and a converting means converting the signal from the above mentioned imaging means to a signal adapted to be transmitted by the above mentioned isolating means and delivering it to the above mentioned isolating means. The above mentioned converting means is a modulating means or A/D converting means. Further, the electronic endoscope apparatus of the present invention is provided with noise reducing means in the front step of the above mentioned converting means.

The other features and advantages of the present invention will become apparent enough with the following explanation.

BRIEF DESCRIPTION OF THE DRAWINGS

FIG. 1 is a block diagram showing the formation of an electronic endoscope apparatus.

FIG. 2 is a side view showing the entire electronic endoscope apparatus.

FIG. 3 is a circuit diagram showing a transformer as an isolating device.

FIG. 4 is a circuit diagram showing a photocoupler as an isolating device.

FIG. 5 is a circuit diagram showing a light transmitting means using optical fibers as an isolating device.

FIGS. 6 and 7 relate to the second embodiment of the present invention.

FIG. 6 is a block diagram showing the formation of an electronic endoscope apparatus.

FIGS. 9 and 10 relate to the fourth embodiment of the present invention.

FIG. 9 is a block diagram showing the formation of an electronic endoscope apparatus.

FIGS. 10A and 10B are waveform diagrams showing respectively color difference signals.

DETAILED DESCRIPTION OF THE PREFERRED EMBODIMENTS

Figure 2:
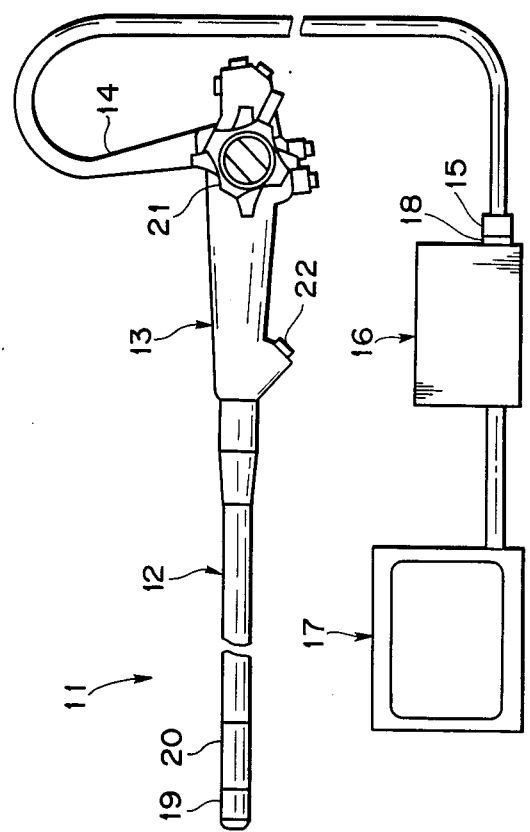

As shown in FIG. 2, an electronic endoscope 11 is provided with an elongate, for example, flexible insertable part 12 to the rear end of which thick operating part 13 is connected. A flexible universal cord 14 is extended sidewise from the rear end part of the above mentioned operating part 13 and is provided with a connector 15 at the tip. This connector 15 is to be connected to a connector receptacle 18 of a video processor 16 containing a light source apparatus and video signal processing circuit. The above mentioned video processor 16 is to be connected to a color monitor 17.

On the tip side of the above mentioned insertable part 12, a rigid tip part 19 and a curvable part 20 adjacent to this tip part 19 and curable rearward are sequentially provided. The above mentioned operating part 13 is provided with a curving operation knob 21 so that, by rotating this curving operation knob 21, the above mentioned curvable part 20 can be curved vertically 1 to the right and left directions. The above mentioned operating part 13 is provided with an inserting part 22 communicating with a treating tool channel provided within the above mentioned insertable part 12.

Figure 1:
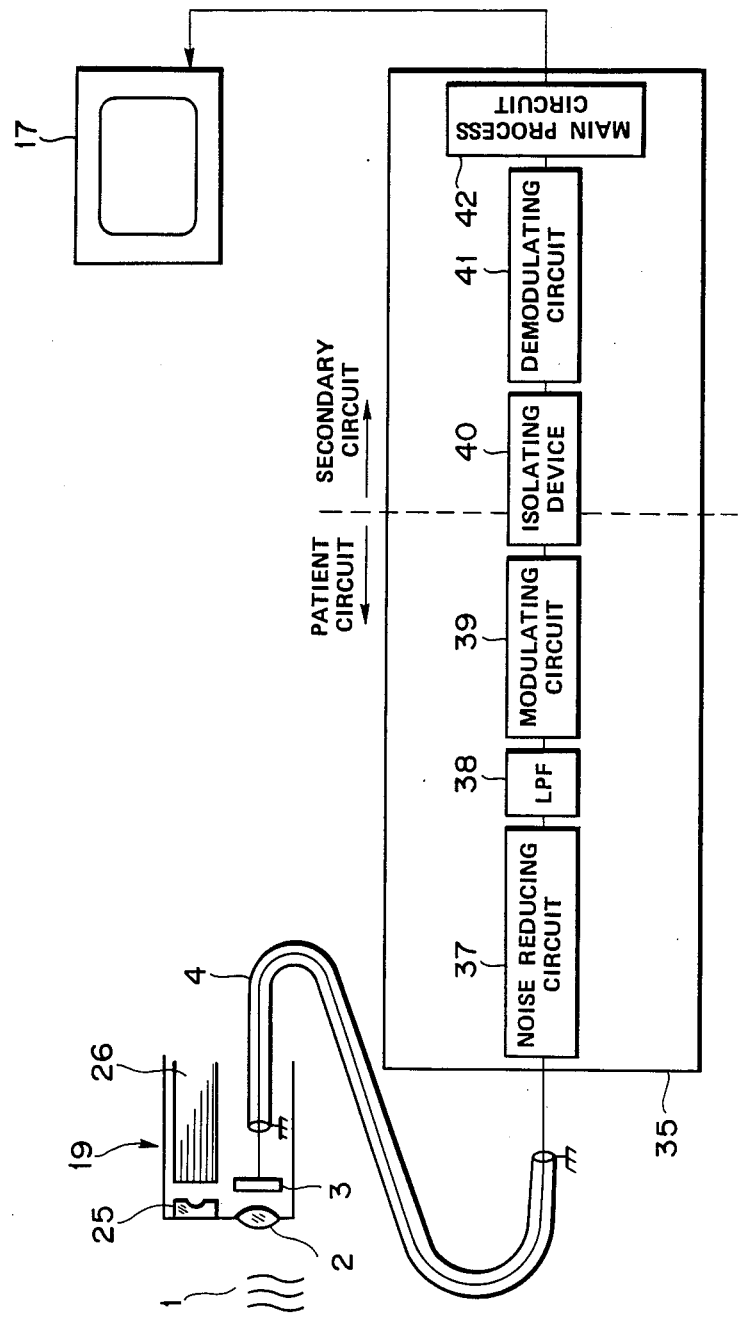
FIGS. 1 to 5 relate to the first embodiment of the present invention.

As shown in FIG. 1, in the above mentioned tip part 19, an image forming optical system 2 is provided and has a solid state imaging device 3 as an imaging means arranged in the image forming position. Here, the solid state imaging device 3 includes a CCD (charge coupled device) and MOS type solid state imaging device. A signal transmitting and receiving cable 4 is connected to the above mentioned solid state imaging device 3, is inserted through the above mentioned insertable part 12 and universal cord 14, is connected to the above mentioned connector 15 and is connected through this connector 15 and connector receptacle 18 to a video signal processing circuit 35 contained in the above mentioned video processor 16. By the way, in case a synchronous system is used for the color imaging system, a color fiber array in which color filters respectively transmitting the color lights of red (R), green (G) and blue (B) are arranged in the mosaic form is provided on the front surface of the above mentioned solid state imaging device 3. In the above mentioned tip part 19, a light distributing lens 25 is provided and a light guide 26 is connected to the rear end side of this light distributing lens 25. This light guide 26 is inserted through the above mentioned insertable part 12 and universal cord 14 and is connected to the above mentioned connector 15. The illuminating light emitted from a light source apparatus not illustrated contained in the above mentioned video processor 16 enters the entrance end of the above mentioned light guide 26, is led to the tip part 19 by this light guide 26, is emitted from the exit end and is radiated onto an object 1 to be imaged through the light distributing lens 25. By the way, in case a frame sequential system is used for the color imaging system, a light source apparatus emitting such frame sequential illuminating lights as of R, G and B is used for the above mentioned light source apparatus.

The light returning from the above mentioned object 1 is made to form an image on the solid state imaging device 3. This object image is photoelectrically converted by the solid state imaging device 3 and is delivered as a video signal to the above mentioned processing circuit 35 through the cable 4. In this video signal processing circuit 35, the above mentioned video signal has such noise reducing measures as a correlated double sampling applied in the noise reducing circuit 37.

The output signal of the above mentioned noise reducing circuit 37 is passed through a low-pass filter 38 to have the component of only the base band of the video signal taken out. The output signal of this low-pass filter 38 is modulated by a modulating circuit 39. The modulating system is such sine wave modulation as an amplitude modulation (AM), frequency modulation (FM) or phase modulation (PM), such pulse modulation as a pulse amplitude modulation (PAM), pulse frequency modulation (PFM), pulse position modulation (PPM) or pulse width modulation (PWM) or such digital modulation as a pulse cord modulation (PCM), difference PCM (DPCM), pulse number modulation (PNM). Any modulation system will do. In the case of transmitting a plurality of kinds of signals, a composite modulating system combining different modulating systems may be used.

Figure 3:
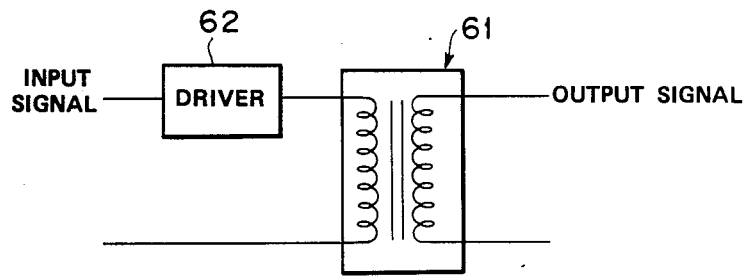
Figure 4:
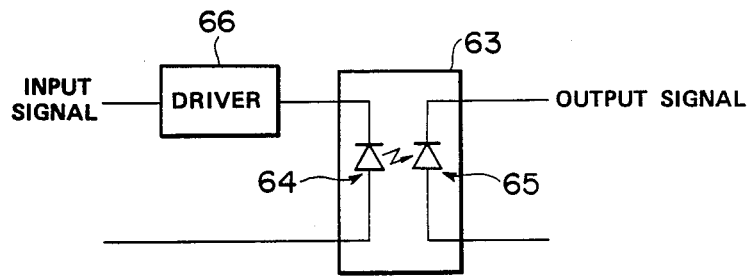

The signal modulated by the above mentioned modulating circuit 39 is transmitted from the patient circuit to the secondary circuit through an isolating device 40. In case the modulating system is, for example, an AM modulation, such high frequency transformer 61 as is shown in FIG. 3 is used. On the primary side of this high frequency transformer 61, a modulation signal is input through a driver 62 and, from the secondary side, the modulation signal is output. For example, in case the modulating system is an FM modulation, the above mentioned high frequency transformer or such high frequency photocoupler 63 as is shown in FIG. 4 is used. The above mentioned photocoupler 63 has an LD 64 and photodiode (which may be a phototransistor) 65. The above mentioned modulation signal is input into the above mentioned LED 64 through a driver 66 and is converted to a photosignal by this LED 64. The light of the above mentioned LED 64 is received is converted to an electric signal and is output.

Figure 5:
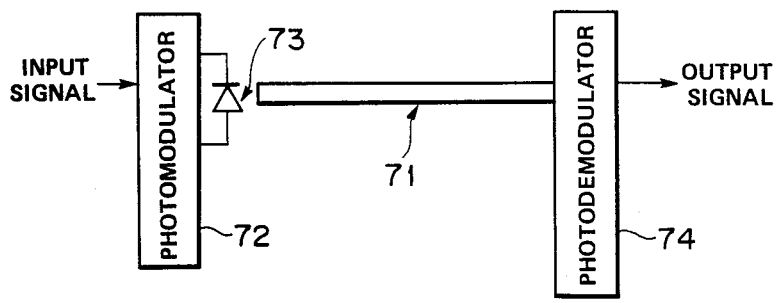

The above mentioned isolating device 40 may be such using optical fibers 71 as in shown in FIG. 5. In this case, the above mentioned modulation signal is input into photomodulator 72, the light modulated by the above mentioned photomodulator 72 is emitted, for example, from an LED 73, enters the entrance end of the optical fibers 71, is emitted from the exit end of the optical fibers 71, is input into a photodemodulator, is converted to an electric signal in this photodemodulator 74 and is output.

The above mentioned isolating device 40 can endure a high voltage of at least 4 Kv, for example, on the basis of the safety standards for medical devices is preferably used.

The isolated signal output from the above mentioned isolating device 40 is demodulated to the original signal by the demodulator, is transmitted to the main processing circuit 42 and is applied to a predetermined signal process and a video signal from this main processing circuit 42 is input into a monitor 17. The object image is displayed by this monitor 17.

Thus, according to this embodiment, after the video signal is modulated, an isolation is made, therefore without deteriorating the picture quality, the patient circuit side and secondary circuit can be positively isolated from each other. Further, as the isolating process can be made after the noises are reduced, the noise reducing process of the solid state imaging device output can be positively made.

Figure 6:
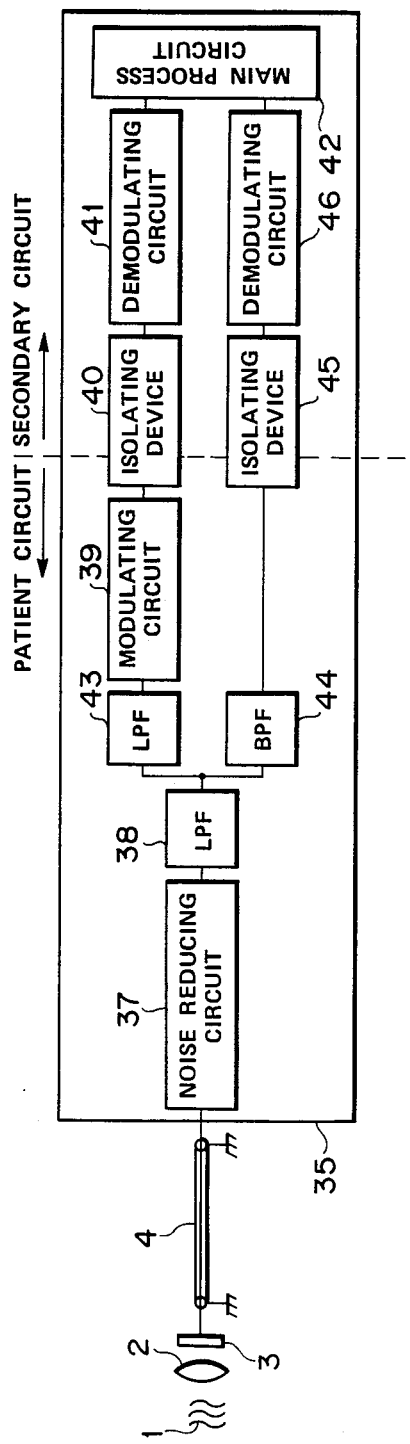

FIGS. 6 and 7 show the second embodiment of the present invention.

This embodiment shows an example of an electronic endoscope apparatus wherein a color difference line sequential system color CCD is used.

Figure 7A:
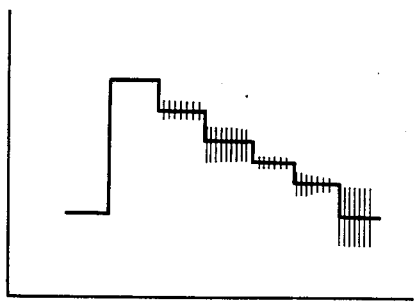
FIG. 7A is a waveform diagram showing a base band of an output signal of a solid state imaging device.
Figure 7B:
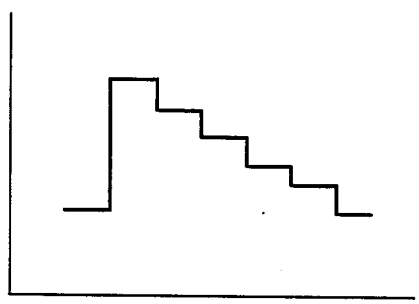
FIG. 7B is a waveform diagram showing a luminance signal.
Figure 7C:
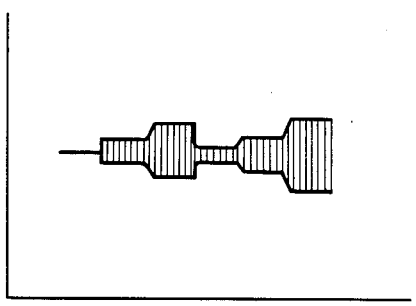
FIG. 7C is a waveform diagram showing a color carrier.

By the way, the same reference numerally are attached to the same circuits as in FIG. 1. Here, the component of only the base band of the output signal from which unnecessary components have been removed through the low-pass filter 38 is such luminance signal on which a color carrier is overlapped as is shown in FIG. 7A. This signal is separated into a luminance signal (FIG. 7B) and color carrier (FIG. 7C) by the low-pass filter 43 and band-pass filter 44. This luminance signal is modulated by the modulating circuit 39 the same as in the first embodiment and is transmitted to the secondary circuit from the patient circuit through the isolating device 40. The isolated luminance signal is likewise demodulated by the demodulating circuit 41 and is transmitted to the main processing circuit 42. On the other hand, the color carrier signal is a color difference signal as balance modulated, is therefore input as it is into the isolating device 45 and is transmitted to the secondary circuit from the patient circuit. In this case, a high frequency transformer is used for the isolating device. The isolated color carrier signal is demodulated by the demodulating circuit 46 and is transmitted to the main processing circuit 42 and is processed together with the above mentioned luminance signal.

The other formations, operations and effects are the same as in the first embodiment.

Figure 8:
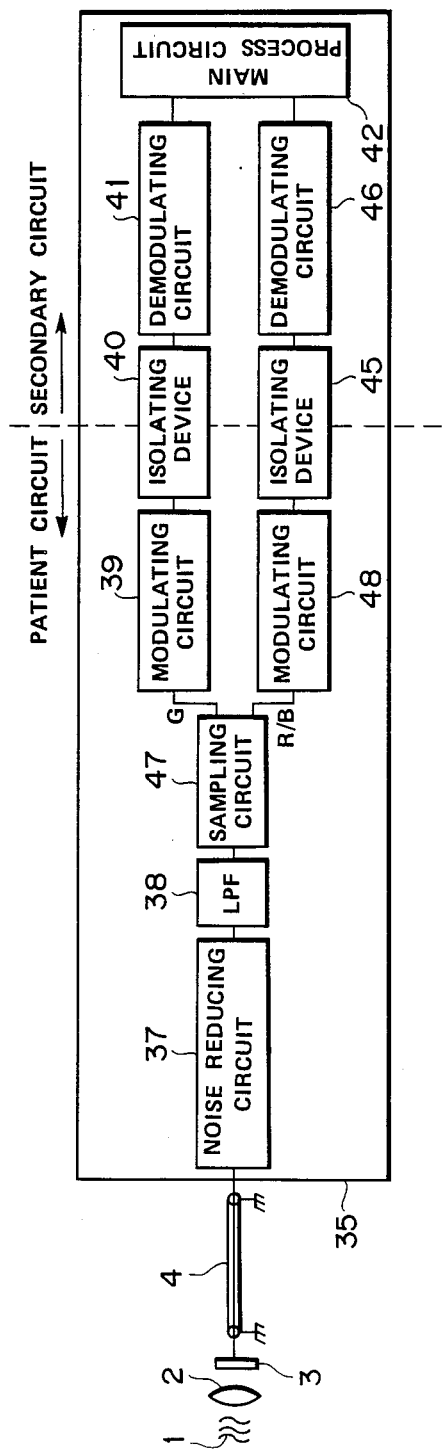
FIG. 8 is a block diagram showing the formation of an electronic endoscope apparatus of the third embodiment of the present invention.

FIG. 8 shows the third embodiment of the present invention.

This embodiment is an example of an electronic endoscope wherein is used a color CCD of a system of obtaining color information by sampling. The output of the CCD 3 passes through the noise reducing circuit 37 and is separated into respective color signals by the sampling circuit 47. Here, in case the arrangement of the color filters of the CCD 3 is like the Bayer arrangement in which the informations of R and B are obtained in each line, the signals will be a G signal and sequentialized R/B signal. Here, the G signal is modulated by the modulating circuit 39 the same as in the first embodiment and is transmitted to the secondary circuit from the patient circuit through the isolating device 40. On the other hand, the sequentialized R/B signal is also modulated by the modulating circuit 48 in the same manner and is transmitted to the secondary circuit from the patient circuit through the isolating device 45. In the secondary circuit, the G signal and R/B signal are demodulated respectively by the demodulating circuits 41 and 46 and are transmitted to the main processing circuit 42 to be processed the same.

The other formations, operations and effects are the same as in the first embodiment.

Figure 9:
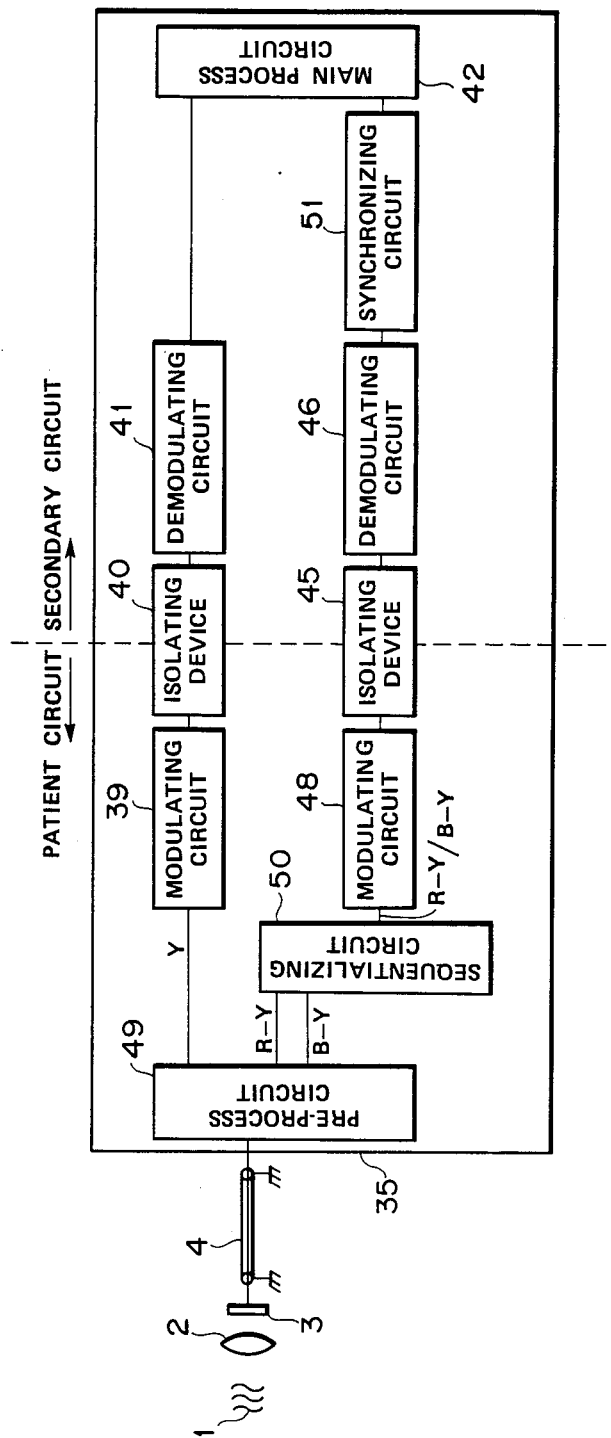

FIGS. 9 and 10 show the fourth embodiment of the present invention.

Figure 10C:
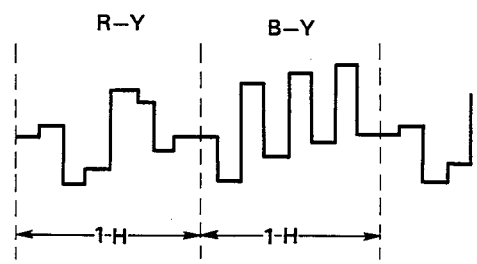
FIG. 10C is a waveform diagram showing sequentialized color difference signals.

Generally, the band of the color difference signal obtained from the solid state imaging device colorized by the color filter array is about f=0.5 MHz. Therefore, as shown in FIG. 10A, in the vertical direction, the same color difference signal for 2H periods is sufficient. Therefore, the electronic endoscope apparatus of a system of sequentializing and isolating the color difference signal is shown as the fourth embodiment in FIG. 9. The output of the solid state imaging device 3 is transmitted to the video signal processing circuit 35 through the cable 4. The luminance signal Y and color difference signals R-Y and B-Y are finally obtained by the pre-processing circuit 49 from the video signal. Here, the color difference signals R-Y and B-Y become such sequentialized signals as are shown in FIG. 10C in the sequentialized circuit 50. Therefore, the same as in the above described embodiment 3, the luminance signal and color difference signals are modulated respectively by the modulating circuits 39 and 48 and are transmitted to the secondary circuit from the patient circuit respectively through the isolating devices 40 and 45. The luminance signal is demodulated by the demodulating circuit 41 and is transmitted to the main processing circuit 42. On the other hand, the color difference signals are demodulated by the demodulating circuit 46, are then synchronized by the synchronizing circuit 51, are transmitted to the main processing circuit 42 and are processed together with the above mentioned luminance signal.

Here, even if the color difference signals are not made sequential, the isolation will be possible. In such case, the modulating circuit, demodulating circuit and isolating device will increase by one.

The other formation, operations and effects are the same as in the first embodiment.

Figure 11:
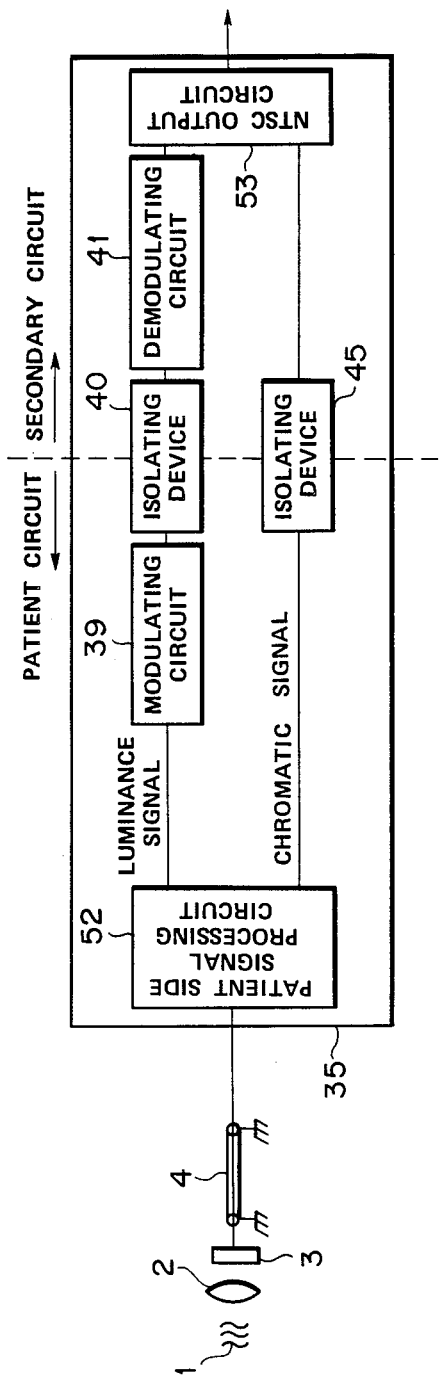
FIG. 11 is a block diagram showing the formation of an electronic endoscope apparatus of the fifth embodiment of the present invention.

FIG. 11 shows the fifth embodiment of the present invention.

This embodiment is an example of using a system in which the color difference signals are modulated at right angles and are then isolated.

In this embodiment, the output of the solid state imaging device 3 is transmitted to the video signal processing circuit 35 through the cable 4. The video signal is converted to a final luminance signal and a chromatic signal modulated at right angles. The luminance signal is modulated by the modulating circuit 39 the same as in the first embodiment and is transmitted to the secondary circuit side through the isolating device 40. The chromatic signal is transmitted as it is to the secondary circuit side through the isolating device 45. The luminance signal is demodulated by the demodulating circuit 41 and is synthesized with a synchronous signal and the above mentioned chromatic signal in the NTSC output circuit 53 and is made an NTSC signal to be output.

The other formations, operations and effects are the same as in the first embodiment.

Thus, according to the first to fifth embodiments, there are effects that, on the patient circuit side, noises can be positively reduced and further, the patient circuit side and secondary circuit side can be well isolated from each other.

Also, in the pre-signal processing circuit receiving the solid state imaging device output, various signals and timing pulses can be processed positively and, particularly, in case a mosaic color filter system color solid state imaging device is used, the luminance and color signals can be generated comparatively easily.

Figure 12:
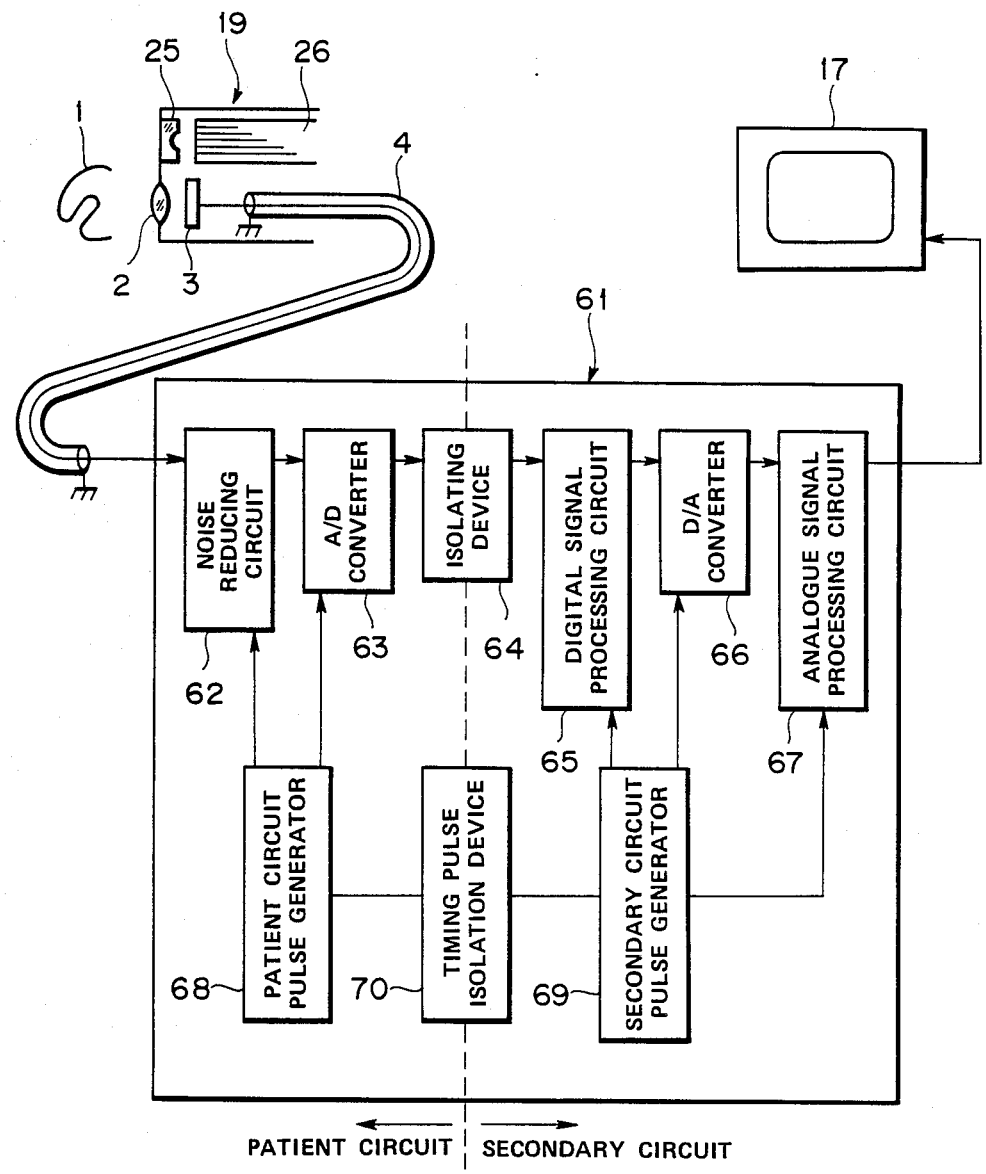
FIG. 12 is a block diagram showing the formation of an electronic endoscope of the sixth embodiment of the present invention.

FIG. 12 shows the sixth embodiment of the present invention.

In this embodiment, the light returning from the object 1 is made to form a image on the solid state imaging device 3. This object image is photoelectrically converted by the solid state imaging device 3 and is delivered as a video signal to the video signal processing circuit 61 through the cable 4. In this video signal processing circuit 61, the above mentioned video signal is first subjected to such noise reducing measures as the correlated double sampling in the noise reducing circuit 62. The output of this noise reducing circuit 62 is sample-held for each pixel. The output of the above mentioned noise reducing circuit 62 is A/D converted at the pixel read-out period by the A/D converter 63. That is to say, by this A/D converter 63, the information of the respective pixels of the solid state imaging device 3 is converted to a digital information. The video signal converted to this digital signal is transmitted to the secondary circuit from the patient circuit through the isolating device 64.

This isolating device 64 is a photocoupler or pulse transformer. The digital signal transmitted to the secondary circuit by the above mentioned isolating device 64 is processed as predetermined by the digital signal processing circuit 65 and is then converted to an analogue signal by the D/A converter 66. The video signal from this analogue signal processing circuit 67 is output to the color monitor 17 or the like. The above mentioned digital signal processing circuit 65 includes, for example, a memory function used to make the picture image stationary.

The patient circuit pulse generator connected to the noise reducing circuit 62 and A/D converter 64 and the secondary circuit pulse generator 69 connected to the digital signal processing circuit 65, D/A converter 66 and analogue signal processing circuit 67 are connected with each other through the timing pulse isolating device 70. Various pulses generated from the above mentioned patient circuit pulse generator 68 and secondary circuit pulse generator 69 are timed by the signal transmitted through this timing pulse isolating device 70.

By the way, this embodiment can be applied to both of the frame sequential system and synchronous system by making the digital signal processing circuit 65 and analogue signal processing circuit 67 correspond to the frame sequential system or synchronous system. Also, in the case of the frame sequential system, the above mentioned digital signal processing circuit 65 may be provided with frame memories corresponding to the respective colors of R, G and B.

Thus, according to this embodiment, the video signal from the solid state imaging device 3 is converted to a digital signal and is isolated. Therefore, no noise mixes in, the picture quality does not deteriorate and the patient circuit sidle and secondary circuit side can be isolated from each other.

Also, as the signal having passed through the noise reducing circuit 62 is A/D converted, the noises are less.

The other formations, operations and effects are the same as in the first embodiment.

Figure 13:
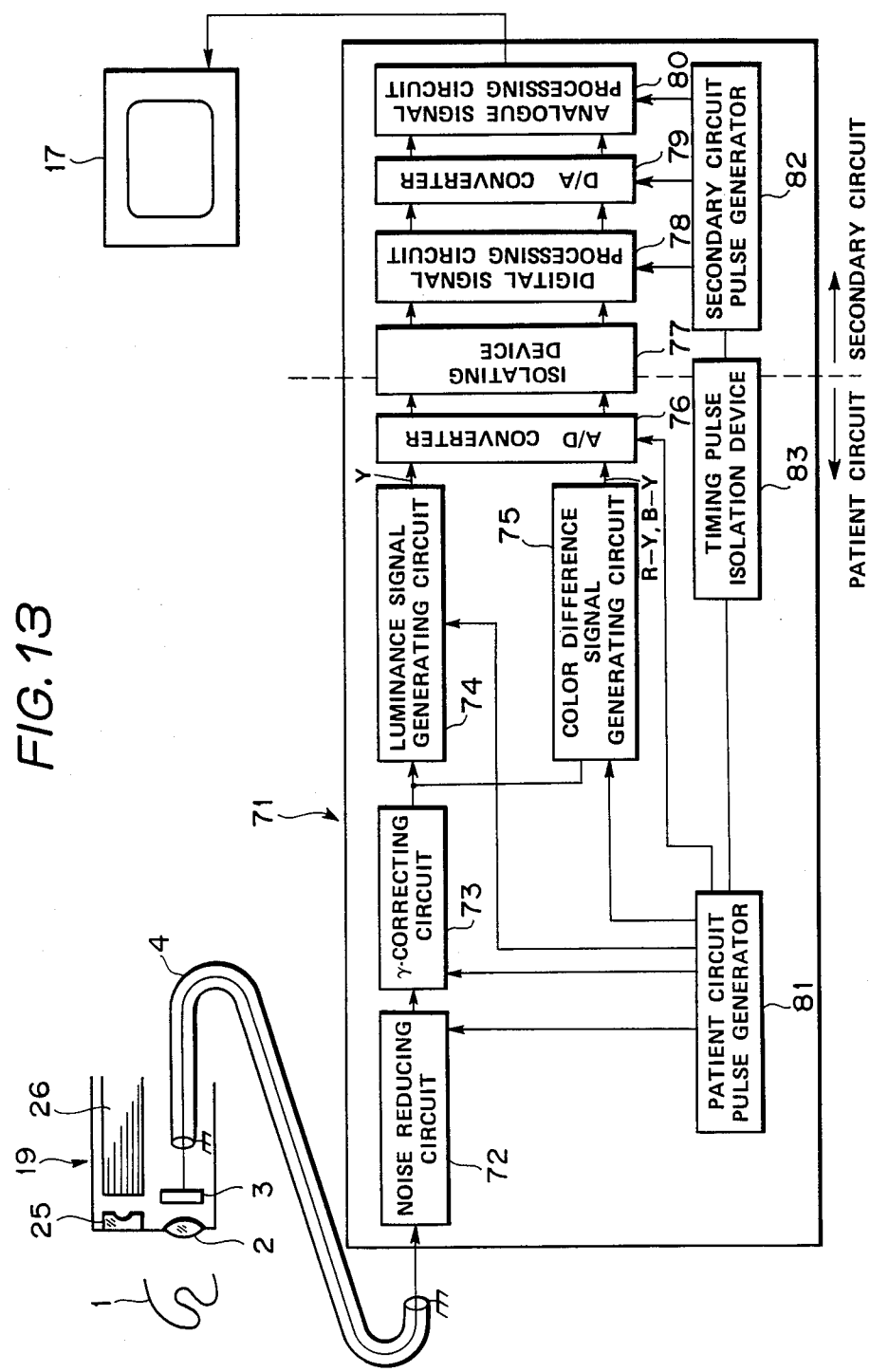
FIG. 13 is a block diagram showing the formation of an electronic endoscope apparatus of the seventh embodiment of the present invention.
Figure 14:
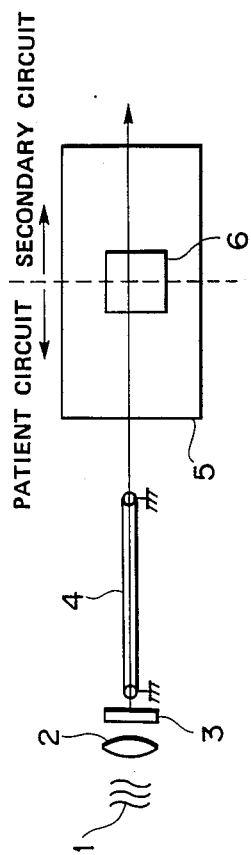
FIG. 14 is a block diagram showing the formation of an electronic endoscope apparatus of the related art.

FIG. 13 shows the seventh embodiment of the present invention.

This embodiment is an example of the case of using the synchronous type for the color imaging system. A filter array is provided on the front surface of the solid state imaging device 3.

In this embodiment, the output of the solid state imaging device 3 is delivered to the video signal processing circuit 71 through the cable 4. In this video signal processing circuit 71, the output signal of the above mentioned solid state imaging device 3 is subjected to noise reducing measures in a noise reducing circuit 72 and is γ-corrected by a γ-correcting circuit 73. The output of this γ-correcting circuit 73 is input into a luminance signal generating circuit 74 and color difference signal generating circuit 75. A luminance signal Y is produced in the luminance signal generating circuit 74 and sequentialized color difference signals R-Y and B-Y are produced in the color difference signal generating circuit 75. These luminance signal Y and color difference signals R-Y and B-Y are respectively converted to digital signals by an A/D converter 76. This digital signal is transmitted to the secondary circuit from the patient circuit through an isolating device 77. The digital signal transmitted to the secondary circuit is converted to an analogue luminance signal Y and color difference signals R-Y and B-Y. This analogue luminance signal Y and color difference signals R-Y and B-Y are input into an analogue signal processing circuit 80, are processed as determined and are then output. The patient circuit pulse generator 51 connected to the noise reducing circuit 72, γ-correcting circuit 73, luminance signal generating circuit 74, color difference signal generating circuit 75 and A/D converter 76 and the secondary circuit pulse generator 82 connected to the digital signal processing circuit 78, D/A converter 79 and analogue signal processing circuit are connected with each other through a timing pulse isolating device 83. By the signal transmitted through this timing pulse isolating device 83, various pulses generated from the above mentioned patient pulse generator 81 and secondary circuit pulse generator 82 are timed.

The other formations are the same as of the sixth embodiment.

According to this embodiment, as the band of the color difference signal is about 0.5 MHz, the sampling frequency of the color signal can be made low for the luminance signal and the capacity of the memory or the like within the digital signal processing circuit 78 can be also made small.

The other operations and effects are the same as in the sixth embodiment.

By the way, in the sixth and seventh embodiments, the isolating devices 64 and 77 are provided just after the A/D converter 63 and 76 but may be provided in any position of the digital signal part between the A/D converters 63 and 76 and D/A converters 66 and 79.

Thus, according to the sixth and seventh embodiments, the signal from the imaging means is converted to a digital signal and is then transmitted to the secondary circuit system by the isolating means and therefore there are effects that less noises are mixed in and the patient circuit side and secondary circuit side can be isolated from each other.

By the way, the present invention can be applied not only to an electronic endoscope wherein a solid state imaging device is arranged in the tip part of the insertable part but also to an endoscope apparatus used with an externally fitted television camera connected to the eyepiece part of such endoscope with which a naked eye observation is possible as a fiber scope.

In this invention, it is apparent that working modes different in a wide range can be formed on the basis of this invention without deviating from the spirit and range of the invention. This invention is not limited to its specific working modes except being limited by the appended claims.

What is claimed is:

1. An electronic endoscope apparatus, comprising:
    an endoscope having an imaging means for converting a light information of an object to be imaged to an electric signal; and
    a signal processing means having an isolating means for isolating and transmitting the information from the imaging means from a patient circuit side to a secondary circuit side, and a converting means for converting the signal from said imaging means to a signal adapted to be transmitted by said isolating means and delivering the adapted signal to said isolating means, and processing the output signal of said imaging means.

2. An electronic endoscope apparatus according to claim 1 wherein said converting means has a modulating means modulating the signal from said imaging means.

3. An electronic endoscope apparatus according to claim 1 wherein said converting means has an A/D converting means A/D converting the signal from the above mentioned imaging means.

4. An electronic endoscope apparatus according to claim 1, 2 or 3 further having a noise reducing means for delivering a noise reduced signal to said converting means.

5. An electronic endoscope apparatus according to claim 4 wherein said noise reducing means is a correlated double sampling circuit.

6. An electronic endoscope apparatus according to claim 1 wherein said isolating means is a high frequency transformer.

7. An electronic endoscope apparatus according to claim 1 wherein said isolating means is a photocoupler.

8. An electronic endoscope apparatus according to claim 1 wherein said isolating means is a light transmitting means using a light conductor.

9. An electronic endoscope apparatus according to claim 8 wherein said light conductor is an optical fiber.

10. An electronic endoscope apparatus according to claim 1 wherein said isolating means is a pulse transformer.

11. An electronic endoscope apparatus according to claim 1 wherein said isolating means is high in the pressure proofness on the basis of the safety standard of medical devices.

12. An electronic endoscope according to claim 11 wherein said isolating means can endure a high voltage of at least 4 Kv.

13. An electronic endoscope according to claim 2 further having a demodulating means taking out the original information from the modulated signal transmitted through the isolating means.

14. An electronic endoscope apparatus according to claim 2 wherein said signal processing means has a means of separating a lumin signal and color carrier from the base band of the output signal of said imaging means and said modulating means modulates said luminance signal.

15. An electronic endoscope apparatus according to claim 2 wherein said signal processing means has a means of separating respective color signals from the output signal of said imaging means and said modulating means is to modulate said respective color signals.

16. An electronic endoscope apparatus according to claim 2 wherein said signal processing means has a means of producing a luminance signal and two color difference signals from the output signal of said imaging means and a means of sequentializing said two color difference signals and said modulating means modulates said luminance signal and sequentialized color difference signals.

17. An electronic endoscope apparatus according to claim 2 wherein said signal processing means has a means of producing a luminance signal and two color difference signals from the output signal of said imaging means and a means of modulating at right angles-said two color difference signals and said modulating means modulates said luminance signal.

18. An electronic endoscope apparatus according to claim 3 further having a D/A converting means for D/A converting the digital signal transmitted through said isolating means.

19. An electronic endoscope apparatus according to claim 18 wherein said signal processing means has a digital signal processing means provided between said A/D converting means and said D/A converting means and an analogue signal processing means provided in the rear step of the above mentioned D/A converting means.

20. An electronic endoscope apparatus according to claim 3 further comprising an isolating means isolating the patient circuit side and secondary circuit side from each other and transmitting timing pulses.

21. An electronic endoscope apparatus according to claim 3 wherein said signal processing means has a means of producing a luminance signal and sequentialized color difference signals from the output signal of said imaging means and said A/D converting means A/D converts respectively said luminance signal and sequentialized color difference signals.

* * * * *

UNITED STATES PATENT AND TRADEMARK OFFICE
CERTIFICATE OF CORRECTION

PATENT NO.  : 4,853,772

DATED       : August 1, 1989

INVENTOR(S) : Kenichi KIKUCHI

It is certified that error appears in the above-identified patent and that said Letters Patent is hereby corrected as shown below:

On the cover page, Item [30], "Feb. 26, 1988" should read --Feb. 26, 1987--.

Signed and Sealed this

Twenty-first Day of August, 1990

Attest:

HARRY F. MANBECK, JR.

*Attesting Officer*  *Commissioner of Patents and Trademarks*